United States Patent [19]
Drennen

[11] Patent Number: 4,905,714
[45] Date of Patent: Mar. 6, 1990

[54] TEETHING DEVICE FOR HOLDING INFANT TEETHING TOYS

[76] Inventor: Barbara R. Drennen, 4080C Guadalcanal Ave., Ewa Beach, Hi. 96706

[21] Appl. No.: 143,935

[22] Filed: Jan. 14, 1988

[51] Int. Cl.[4] .......... A61F 13/00
[52] U.S. Cl. .......... 128/878; D2/229; 128/DIG. 15
[58] Field of Search .......... D2/229, 226, 227, 228; 128/DIG. 26, 359, 360, 878, 877, 879, 882, DIG. 15; 604/179, 180; 2/48, 49 R

[56] References Cited

U.S. PATENT DOCUMENTS

| | | | |
|---|---|---|---|
| D. 160,140 | 9/1950 | Binney | D24/45 |
| D. 280,749 | 9/1985 | Thomson | D24/45 |
| D. 288,849 | 3/1987 | Williams et al. | D24/45 |
| 2,595,462 | 5/1952 | Johnson | D24/45 |
| 2,827,055 | 3/1958 | Cardin | D24/45 |
| 2,988,745 | 6/1961 | Whitley et al. | 2/48 |
| 3,789,842 | 2/1974 | Froimson | 128/DIG. 15 |
| 4,074,397 | 2/1978 | Rosin | 128/DIG. 15 |
| 4,481,942 | 11/1984 | Duncan | 128/878 |
| 4,484,914 | 11/1984 | Brown | 604/180 |
| 4,590,931 | 5/1986 | Kidwell, Jr. | 128/DIG. 15 |
| 4,591,356 | 5/1986 | Christie | 604/179 |
| 4,646,365 | 3/1987 | Suprise et al. | 2/49 R |

*Primary Examiner*—Max Hindenburg
*Assistant Examiner*—Scott Getzow
*Attorney, Agent, or Firm*—Jerry T. Kearns

[57] ABSTRACT

A teething device is formed from a fabric square approximately twelve inches in width. On one side of the fabric square, four fabric loops are secured. One end of each loop is sewn to the fabric square and an opposite end of each loop is secured to the fabric square by cooperating VELCRO fasteners. One fastening loop is positioned adjacent each corner of the fabric square. An elongated narrow cloth leash extends from one corner of the fabric square. On one side, the leash has a pair of cooperating VELCRO fastening strips for securing the leash around the wrist of a child or to the frame of a stroller. On the opposite side of the leash, an additional VELCRO fastening strip is provided for cooperation with a VELCRO fastening strip positioned on a back side corner of the fabric square. By virtue of this construction, the leash may be optionally utilized to secure the fabric square around the neck of a child, for use as a bib.

1 Claim, 3 Drawing Sheets

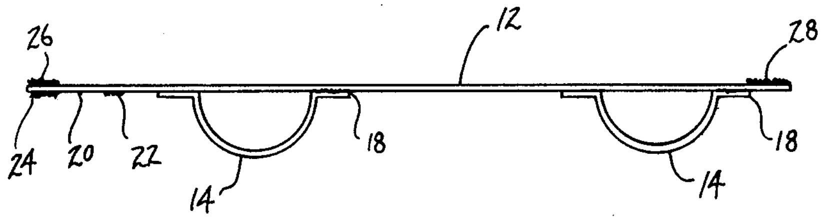
Fig 2
Fig 3
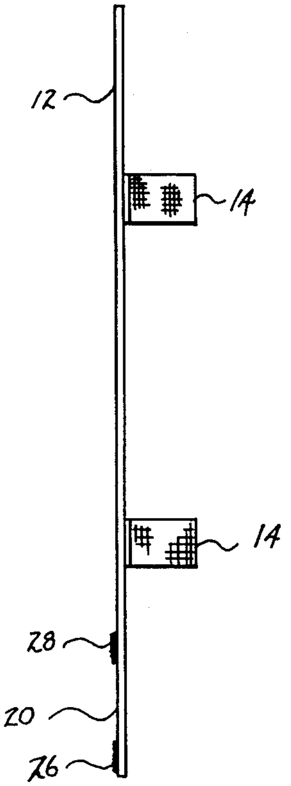

TEETHING DEVICE FOR HOLDING INFANT TEETHING TOYS

BACKGROUND OF THE INVENTION

1. Field of the Invention

The present invention relates to teething devices, and more particularly pertains to a fabric square provided with loop fasteners for holding various teething toys. When infants are teething, they are prone to chew and suck on any available object. While various conventional teething toys are available for use by such infants, these devices are prone to becoming contaminated by falling on the ground. Additionally, such infants prefer to have an assortment of available teething toys. While teething, infants frequently drool on their face, hands and clothes. Conventional teething devices lack any provisions for wiping saliva from teething infants. In order to overcome these problems, the present invention provides a fabric square with a plurality of VELCRO secured loop fasteners for removably retaining an assortment of teething toys.

2. Description of the Prior Art

Various types of teething devices are known in the prior art. A typical example of such a teething device is to be found in U.S. Design Pat. No. 160,140, which issued to H. Binney on Sept. 19, 1950. This patent discloses a plurality of key shaped teething toys retained by a chain. U.S. Design Pat. No. 280,749, which issued to H. Thomson et al on Sept. 24, 1985, discloses a teething toy which resembles a plurality of keys on a key ring. A tag provided on the key ring has an imprinted smiling face. U.S. Design Pat. No. 288,849, which issued to D. Williams et al on Mar. 17, 1987, discloses a teething toy which resembles a fish and is provided with a plurality of circular rings. U.S. Pat. No. 2,595,462, which issued to A. Johnson on May 6, 1952, discloses a teething device for use by infants which comprises a scallop shaped plastic body portion having an attached chain leash for securement around the wrist of an infant. U.S. Pat. No. 2,827,055, which issued to M. Carden on Mar. 18, 1958, discloses a teething device with an attached leash for securement around the wrist of an infant. The teething device has a body portion which may be formed from rubber in the shape of a squirrel.

While the above mentioned devices are suited for their intended usage, none of these devices provide a fabric square with a plurality of VELCRO secured loops for the removable retention of an assortment of teething toys. Additionally, none of the previously described teething devices utilize a fabric square having an attached leash adapted for selectively securing the fabric square around the wrist of an infant, or alternatively around the neck of an infant for use as a bib. Inasmuch as the art is relatively crowded with respect to these various types of teething devices, it can be appreciated that there is a continuing need for and interest in improvements to such teething devices, and in this respect, the present invention addresses this need and interest.

SUMMARY OF THE INVENTION

In view of the foregoing disadvantages inherent in the known types of teething devices now present in the prior art, the present invention provides an improved teething device. As such, the general purpose of the present invention, which will be described subsequently in greater detail, is to provide a new and improved teething device which has all the advantages of the prior art teething devices and none of the disadvantages.

To attain this, a representative embodiment of the concepts of the present invention is illustrated in the drawings and makes use of a fabric square approximately twelve inches in width. On one side of the fabric square, four fabric loops are secured. One end of each loop is stitched to the fabric square and an opposite end of each loop is secured to the fabric square by a hook and loop type fastener of the type sold under the trademark VELCRO. One fastening loop is positioned adjacent each corner of the fabric square. An elongated narrow cloth leash extends from one corner of the fabric square. On one side, the leash has a pair of cooperating VELCRO fastening strips for securing the leash around the wrist of a child or to the frame of a stroller. On the opposite side of the leash, an additional VELCRO fastening strip is provided for cooperation with a VELCRO fastening strip positioned on a back side corner of the fabric square. By virtue of this construction, the leash may be optionally utilized to secure the fabric square around the neck of a child, for use as a bib. The fabric square may be formed from a poly-cotton material, terry cloth, felt or a 100% cotton material. In use, various teething toys are secured by the loop fasteners for use by infants. These teething toys are thus prevented from falling onto the ground and becoming contaminated. Additionally, the fabric square is useful as a wiping cloth for cleaning the hands and face of an infant. The teething toys may be easily removed from the fabric square, to enable machine washing of the fabric square.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved teething device which has all the advantages of the prior art teething devices and none of the disadvantages.

It is another object of the present invention to provide a new and improved teething device which may be easily and efficiently manufactured and marketed.

It is a further object of the present invention to provide a new and improved teething device which is of a durable and reliable construction.

An even further object of the present invention is to provide a new and improved teething device which is susceptible of a low cost of manufacture with regard to both materials and labor, and which accordingly is then susceptible of low prices of sale to the consuming public, thereby making such teething devices economically available to the buying public.

Still yet another object of the present invention is to provide a new and improved teething device which provides in the apparatuses and methods of the prior art some of the advantages thereof, while simultaneously overcoming some of the disadvantages normally associated therewith.

Still another object of the present invention is to provide a new and improved teething device formed from a fabric square having a plurality of VELCRO secured loop fasteners for the removable retention of a plurality of teething toys.

Yet another object of the present invention is to provide a new and improved teething device which makes use of a machine washable fabric square for securing a plurality of teething toys and which may also be utilized for wiping the hands and face of an infant.

Even still another object of the present invention is to provide a new and improved teething device having a fabric square provided with a plurality of VELCRO secured loops for removably retaining various teething toys and provided with an elongated leash for selectively securing the fabric square around the wrist of an infant, or alternatively around the neck of an infant for use as a bib.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top view of the teething device of the present invention.

FIG. 3 is a side view of the teething device of the present invention.

DESCRIPTION OF THE PREFERRED EMBODIMENT

Figure 1:
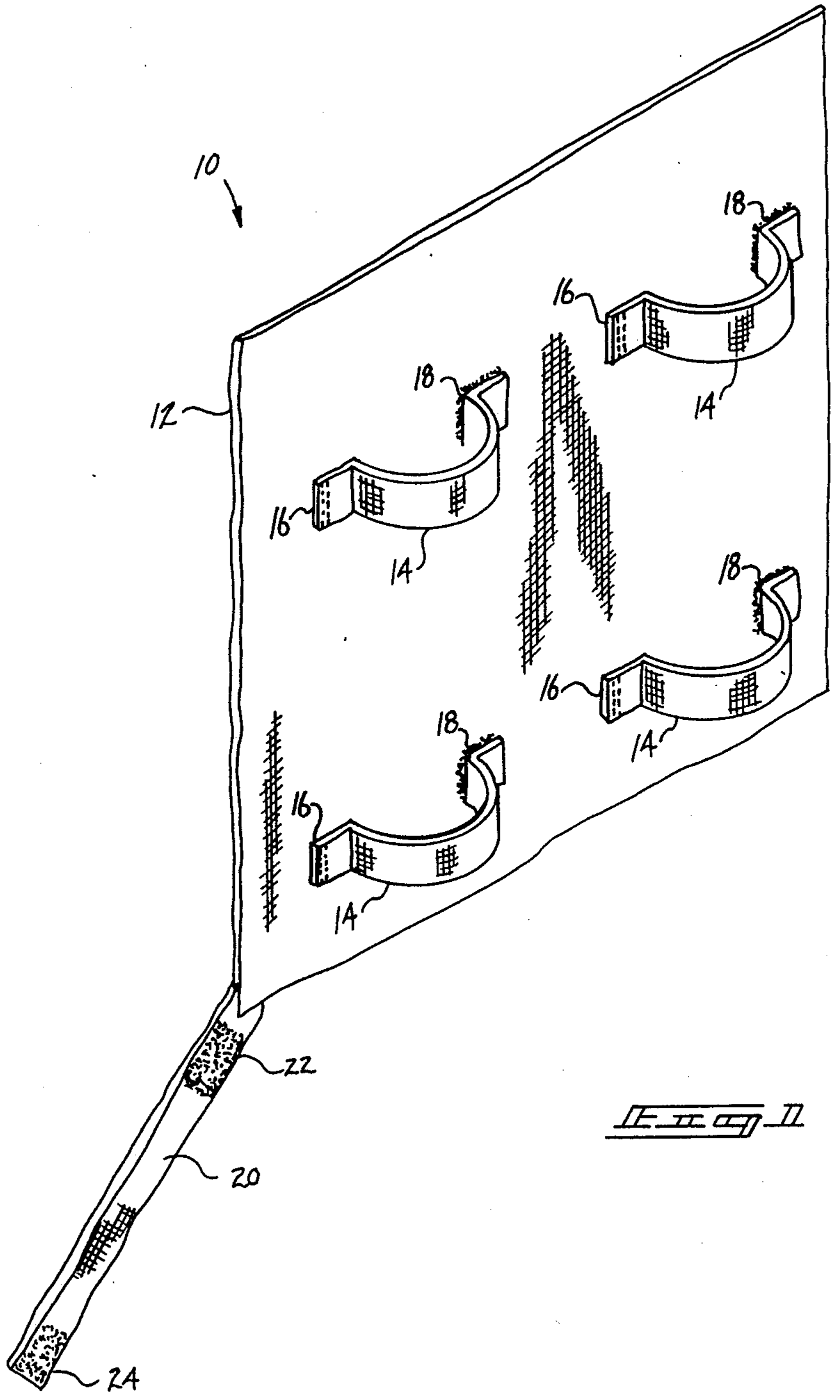
FIG. 1 is a perspective view of the front side of the teething device of the present invention.

With reference now to the drawings, and in particular to FIG. 1 thereof, a new and improved teething device embodying the principles and concepts of the present invention and generally designated by the reference numeral 10 will be described.

More specifically, it will be noted that the first embodiment 10 of the invention includes a square fabric sheet 12. The square fabric sheet 12 is preferably formed from a terry cloth material, a 50% polyester-50% cotton material, a felt material or a 100% cotton material. The sheet 12 has a preferred width of about twelve inches. On a front side of the sheet 12, four loop fasteners 14 are attached. One loop fastener 14 is positioned adjacent each corner of the sheet 12. The loop fasteners 14 are preferably formed from elongated narrow strips of the same fabric material of which the sheet 12 is formed. One end of each of the loop fasteners 14 is sewn at 16 to the square fabric sheet 12. An opposite end of each of the loop fasteners 14 is secured at 18 by cooperating hook and loop type fasteners, of the type sold under the trademark VELCRO, on the loop 14 and the sheet 12. A leash 20, formed from a narrow elongated strip of fabric, is attached at one corner of the sheet 12. A first VELCRO fastening strip 24 is secured to the leash 20, adjacent the free end thereof. A second VELCRO fastening strip 22, for cooperation with the first VELCRO fastening strip 24, is provided on the leash 20, adjacent the sheet 12. By use of the VELCRO fasteners 22 and 24, the leash 20 may be secured around the wrist of an infant, or to a stroller. The loop fasteners 14 may each be utilized to secure a different teething toy to the fabric square sheet 12. Thus, the various teething toys will be secured to the sheet 12, preventing possible contamination from being dropped on the ground. The fabric square 12 may also be utilized as a wiping rag to clean the hands and face of an infant. By removing the various teething toys from the loop fasteners 14, the fabric square 12 may be conveniently machine washed. The fabric sheet 12 may be embroidered or imprinted with a variety of ornamental designs.

With reference now to FIG. 2, a top view of the teething device of the present invention is provided. A third VELCRO fastening strip 26 is provided on a back side of the leash 20, adjacent the free end thereof. A fourth VELCRO fastening strip 28 for cooperation with the third VELCRO fastening strip 26, is provided on the back side of the fabric square 12, adjacent one corner thereof. Through the use of the cooperating VELCRO fasteners 26 and 28, the leash 20 may be utilized to secure the fabric sheet 12 around the neck of an infant for use as a bib.

In FIG. 3, a side view of the teething device of the present invention is provided.

Figure 4:
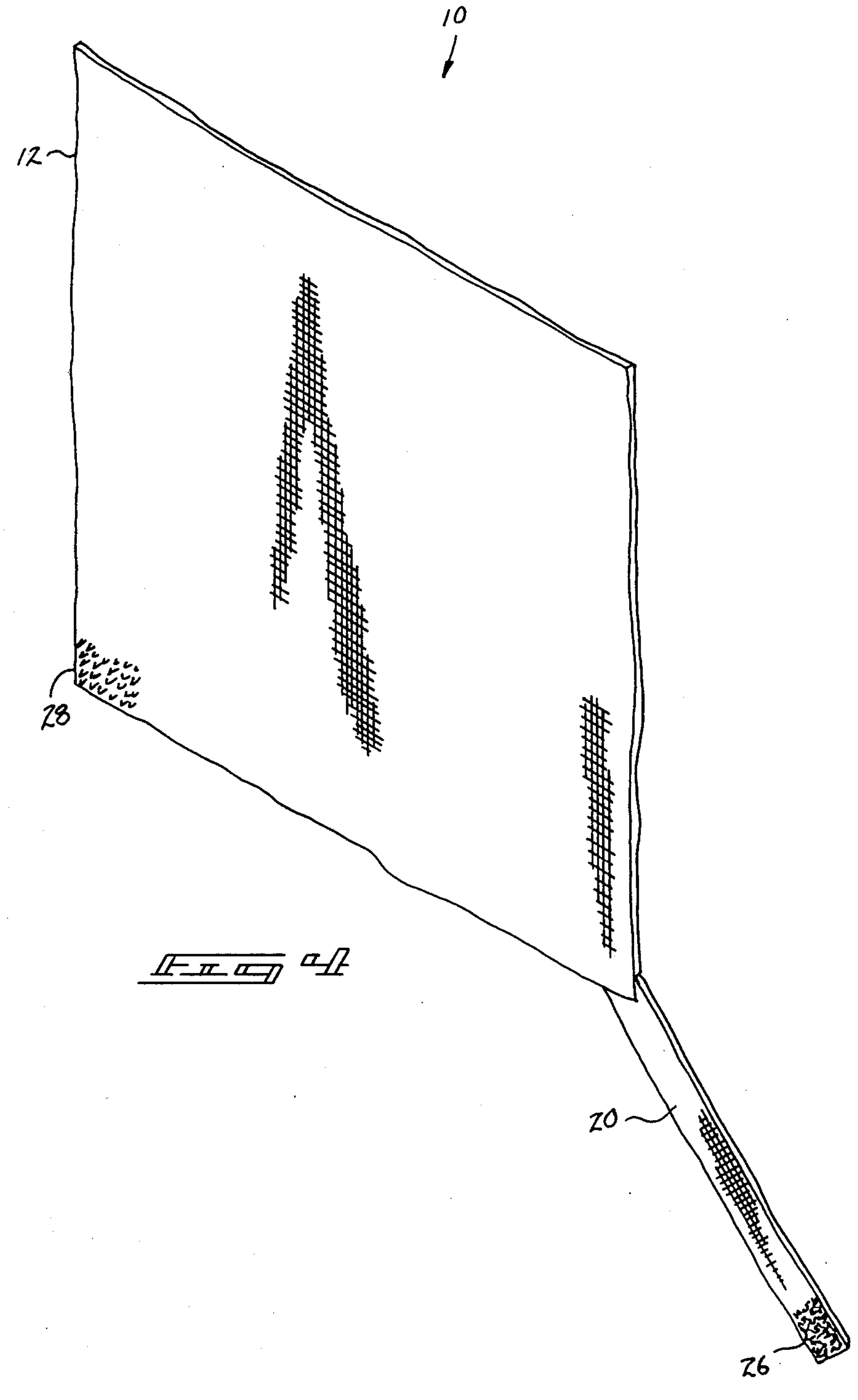
FIG. 4 is a perspective view of the back side of the teething device of the present invention.

In FIG. 4, a perspective view of the teething device of the present invention is provided, illustrating the back side of the fabric square 12 and the leash 20. As may now be readily understood, the leash 20 serves a dual purpose in enabling the fabric square 12 to be secured around the wrist, or around the neck of an infant. Thus, the fabric square 12 may be utilized as a teething device secured to the wrist of an infant, as a bib secured around the neck of an infant, or as a wiping rag for cleaning the hands and face of the infant.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved teething device for holding infant teething toys, comprising:

a fabric square formed from a fabric material;

four fabric loop fasteners on a front side of said fabric square dimensioned for holding infant teething toys;

one of said loop fasteners disposed adjacent each corner of said fabric square;

one end of each of said loop fasteners sewn to said fabric square;

an opposite end of each of said loop fasteners secured by a hook and loop type fasteners to said fabric square;

a narrow elongated fabric leash attached to one corner of said fabric square;

a first hook and loop type fastener on a front side of said leash, adjacent a free end thereof;

a second hook and loop type fastener for cooperation with said first hook and loop type fastener on said front side of said leash, adjacent said fabric square;

a third hook and loop type fastener on a back side of said leash, adjacent said free end; and a fourth hook and loop type fastener for cooperation with said third hook and loop type fastener on a back side of said fabric square, adjacent a corner thereof.

* * * * *